United States Patent [19]

Markarian et al.

[11] Patent Number: 4,818,512
[45] Date of Patent: Apr. 4, 1989

[54] ACTIVATED ALUMINUM CHLORHYDROXIDE

[75] Inventors: Herand M. Markarian, Congers, N.Y.; Allan H. Rosenberg, Randolph; George L. Cohen, Warren, both of N.J.

[73] Assignee: Bristol-Myers Company, New York, N.Y.

[21] Appl. No.: 100,153

[22] Filed: Sep. 23, 1987

[51] Int. Cl.$^4$ .............................................. C01B 7/00
[52] U.S. Cl. .................................... 423/462; 423/629
[58] Field of Search ................................. 423/462, 629

[56] References Cited

U.S. PATENT DOCUMENTS 3,904,741  9/1975  Jones et al. ........................... 423/462
4,359,456  11/1982  Gosling et al. ....................... 423/462

FOREIGN PATENT DOCUMENTS 0183171  4/1986  European Pat. Off. ............ 423/462
1568831  6/1980  United Kingdom ................ 423/462
2048229  12/1980  United Kingdom ................ 423/462

OTHER PUBLICATIONS

*Gel Filtration Theory and Practice* by Pharmacia Fine Chemicals, Uppsala, Sweden.

Primary Examiner—Robert L. Stoll
Assistant Examiner—Paige C. Harvey
Attorney, Agent, or Firm—Sandra M. Person

[57] ABSTRACT

Prepares aluminum chlorhydroxide product high in molecular species content having a $K_d$ value equal to 0.4 by heating a 5% aqueous solution of aluminum chlorhydroxide at a temperature in the range of from about 100° to about 132° for a period of about 30 minutes to about three months and then spray drying the product, the heating preferably being done under pressure.

11 Claims, No Drawings

ACTIVATED ALUMINUM CHLORHYDROXIDE

FIELD OF INVENTION

This invention relates to a process for preparing a highly activated aluminum chlorhydroxide product and to products prepared by such a process. More particularly, it relates to a process (and the corresponding product) for preparing an aluminum chlorhydroxide product which contains a high percentage (i.e. about 85% weight) of a highly active antiperspirant species of aluminum chlorhydroxide sometimes referred to herein by the term SAACH (Super Activated Aluminum Chlorhydroxide).

BACKGROUND

Aluminum chlorhydroxide has been used for a number of years as the active ingredient in antiperspirant compositions. This has been available commercially as a 50% aqueous solution and has been marketed under the trademark CHLORHYDROL. The formula of aluminum chlorhydroxide has been generally given by the structure $Al_2(OH)_5Cl$. However, it has long been realized that at best this structure represented the empirical formula and that aluminum chlorhydroxide is a very complicated material.

More recently it has been discovered that in fact aluminum chlorhydroxide is at least a mixture of molecular species representing different degrees of polymerization of aluminum chlorhydroxide that may correspond to the empirical formula $Al_2(OH)_5Cl$. Moreover, it has been found that the various molecular species do not have the same degree of effectiveness as antiperspirant agents but that as a matter of fact one species is superior to the others in this activity. For reasons that will become more apparent later this species or fraction is identified herein as the $K_d=0.4$ fraction. The present invention is concerned with a process for preparing an aluminum chlorhydroxide product high in the $K_d=0.4$ fraction i.e. of the order up to about 85% by weight of the total aluminum chlorhydroxide product.

THE INVENTION

It has now been found that aluminum chlorhydroxide products having a large component of the most active molecular species (i.e. $K_d=0.4$) can be obtained by heating an aqueous solution containing no more than about 5% by weight of aluminum chlorhydroxide at a temperature of about 100°-132° C. for no longer than about 1 hour and preferably from about 10 minutes to about ½ or 1 hour and, preferably, in a closed vessel under pressure, and then spray drying the resulting reaction products to produce a powdered product containing at least about 80% to about 85% by weight of the $K_d=0.4$ fraction of aluminum chlorhydroxide, the weight percentages being based on the total weight of spray dried product. The variation in the yield is attributed to the variability in the sensitivity of the analytical method used in measuring the concentration of $K_d=0.4$ fraction as well as the variability in the spray drying procedure.

PRIOR ART

A number of attempts have been made in the prior art to produce aluminum chlorhydroxide products containing the more active molecular species of aluminum chlorhydroxide. One such process is described in U.S. patent to Jones et al No. 3,904,741 and involves heating a 50% aqueous solution of aluminum chlorhydroxide at a temperature of from about 100° C. to about 105° C. for a minimum of 1 hour and preferably for between 2 and 4 hours. The product of this reaction is then dried to a solid. The conditions employed in this process are obviously quite different from those employed in the present invention and give significantly different results as will be made more apparent below. Thus the concentration of aluminum chlorhydroxide solution (50%), the time of treatment (1-4 hours) and temperature of treatment (100° C.-105° C.) are each significantly different from those utilized in the present process.

U.S. Pat. No. 4,359,456 relates to a process for producing aluminum chlorhydroxide polymer of increased antiperspirant activity which comprise heating a solution of aluminum chlorhydroxide in a temperature range of from 50° C. to 140° C. for a time period ranging from 0.5 hours to 30 days. However, the concentration range of the aluminum chlorhydroxide used in this process expressed in terms of aluminum is 2.5% to 8.5% which corresponds to a concentration range of 10%-34% expressed as aluminum chlorhydroxide. This is clearly outside the range of concentration employed in the present invention.

In column 2, lines 14-35 of this patent (i.e. U.S. Pat. No. 4,359,456) reference is made to a Russian publication in Izvestiya Akademi Nauk Latvinskoi SSR. This reference concerns an investigation into the effect of time and temperature of heating solutions of aluminum chlorhydrate in the preparation of boehmite, a process totally unrelated to the purposes of the present invention. Although the concentration of aluminum chlorhydroxide solution employed in this process ranges from about 3.29% to about 6.5% and the temperature range is from about 100° C. to 180° C. the time of treatment was 5 hours which is well outside the range of time treatment used in this invention.

U.K. patent application 2,048,229A relates to a process for preparing certain aluminum chlorhydroxide complexes which are said to be efficacious as antiperspirants. The process involves aging solutions of aluminum chlorhydroxide at temperatures below 100° C. (preferably at 90° C. or lower). The concentration range of the aluminum chlorhydrate is said by the patentees to vary from at least 5% by weight and preferably at least 7.5% and, more preferably, 10%. At the 10% concentration level of aluminum chlorhydroxide the time of treatment is given as from 1 week to 8 hours and at a temperature between 50° C.-80° C. These parameters are clearly outside those employed in the process of the present invention. European patent application 0,183,171 relates to a process for preparing an aluminum chlorhydroxide molecular species said to have enhanced activity. This process involves heating an aqueous solution containing about 40 to 50 percent by weight of aluminum chlorhydroxide at a temperature of at least 130° C. for about 1 to 12 hours in a closed vessel. The resultant solution may then be cooled and dried to a solid by spray drying. It can be seen from this that important parameters for practicing the process of the present invention are quite different from those disclosed in this reference.

DETAILED DESCRIPTION OF INVENTION

As indicated previously, the purpose of the present invention is to provide a process that produces an antiperspirant product of aluminum chlorhydroxide containing a high level of a molecular species of aluminum chlorhydroxide (about 85% by weight) that has high antiperspirant activity; this molecular species of aluminum chlorhydroxide is identified by the value $K_d = 0.4$.

The $K_d$ value for a material is a value that is determined by depositing a solution of the material of interest on a gel column, passing an eluant through the column packed with said gel (e.g. Sephadrex G-25) and measuring the elution volume (Ve). The elution volume is characteristic for molecular species that pass through the packed column or bed and is generally measured by measuring the volume of eluant passing out of the column to the point of maximum concentration of the particular molecular species.

$V_e$ is not itself sufficient to define the behaviour of the sample substance since this parameter varies with the total volume of the packed bed $(V_t)$ and with the way the column has been packed. By analogy with other types of partition chromatography the elution of a solute is best characterized by a distribution coefficient $(K_d)$ wherein $$K_d = (V_e - V_o)/V_s$$

in which $v_o$ is the void volume, the elution volume of molecules which are only distributed in the mobile phase because they are larger than the largest pores in the gel. $V_s$, the volume of the stationary phase, in gel filtration is equal to $V_i$, the volume of solvent inside the gel which is available to very small molecules, i.e. the elution volume of a solute which will distribute freely between the mobile and stationary solvent phases minus the void volume. Thus $K_d$ represents the fraction of the stationary phase which is available for diffusion of a given solute species. (See publication entitled *Gel Filtration Theory and Practice* published by Pharmacia Fine Chemicals, of Uppsala, Sweden, and particularly pages 30–32 which is incorporated herein by way of reference).

Using the aforesaid technique at least 4 molecular species of aluminum chlorhydroxide have been identified, namely, species that have $K_d$ values of 0, 0.25, 0.4 and 0.6, respectively. The molecular species of having a $K_d$ value of 0 has the highest molecular weight whereas that with a $K_d$ value of 0.6 has the lowest molecular weight. The species having $K_d$ values of 0.25 and 0.4 are of intermediate molecular weight with that having the value 0.25 being a higher molecular weight than that having the value of 0.4. The species of special interest is the present invention and that found to be the most active antiperspirant is the species having a $K_d$ value of 0.4.

The process of the present invention is carried out using a solution of aluminum chlorhydroxide (that is basic aluminum chloride). A variety of basic aluminum chlorides may be used as starting materials in the practice of the process of this invention. These generally conform to the formula $Al_2(OH)_xCl_{(6-x)}$ wherein $0 < x > 6$ and in which x need not be an integer. However, the best results are obtained with a solution of what is known in this art as 5/6 basic aluminum chloride which corresponds to formula $Al_2(OH)_5Cl$.

It is a feature of a preferred aspect of the present invention to carry out the conversion of the aluminum chlorhydroxide species to the preferred high activity variety under pressure. The pressures at which the conversion may take place in this modification of the invention can be varied. Generally the internal pressure employed will be in the range up to about 35 psig; with the preferred range being from about 25 to about 35 psig. A variety of means and vessels known to those skilled in the chemical arts are available for this purpose.

One such pressurized vessel that has been employed for small scale preparations is the Barnstead Model 1250 Labclave with a temperature range of from 25° C. to 132° C. and a pressure range of 0–29 psig. This vessel has been used in practicing the process of the present invention at a temperature in the range of from about 125° C. to 132° C. and a pressure in the range of from about 27 to about 29 psig. For larger scale preparations, pressure cookers made by Hamilton Kettles, Cincinatti, Ohio; Paul Mueller Company, Springfield, MO; Lee Kettles, Philipsburg, PA., can be employed. The Hamilton Kettles style PC container, for example, has a 150 gallon capacity and is equipped with a propeller agitator and hydraulic lift. This has an internal pressure range of from 0–35 psig and can be operated in the range of up to 35 psig in practicing the present invention.

A further feature of the present invention is to spray-dry the reaction product produced by the heating of aluminum chlorhydroxide solution to produce a powdered product. This is important since if allowed to remain in aqueous solution the product of the conversion will revert back, at least in part, to its prior constituents with the result that there would be a reduction in the desired amount of the highly active aluminum chlorhydroxide molecular species having the $K_d$ value of about 0.4. For the same reason, to retain the desired antiperspirant efficacy of the products made by the process of this invention they will ordinarily not be made up into aqueous systems but rather will be used in non-aqueous system such as those often employed in aerosol antiperspirant products.

A number of techniques will known to those skilled in this art may be employed to spray dry the conversion product in accordance with this invention. In one such procedure the conversion product, which is still in solution and hot, is sprayed into the spray dryer. A spray dryer that has been found to be quite useful for the present purposes in marketed as The BUCHI 190 MINI SPRAY DRYER. The inlet and outlet temperatures employed in the spray drying operation can vary. Generally, the inlet temperatures will be set in the range of from about 150° C. to about 190° C. with the preferred setting being about 170°. The outlet temperature will usually be set in the range of from about 85° C. to about 95° C. with the preferred outlet temperature being about 90° C. The following examples are given to further illustrate the present invention. It is to be understood however, that the invention is not limited thereto.

EXAMPLE 1

Preparation of SAACH Containing About 80–85% $K_d$0.4 Molecular Species

1. To 150 g of 50% aluminum chlorohydrate solution in a 2 liter beaker, add 1350 g distilled water.
2. Place the beaker containing the solution in an autoclave. Set the temperature to 270° F. (132° C.). Autoclave for half an hour.
3. Spray dry the hot solution using a BUCHI 190 Mini Spray Dryer with the following settings:

| | |
|---|---|
| Pump Control | 5 |
| Aspirator | 15 |
| Heating Control | 12 |

| -continued | |
|---|---|
| Flow Indicator | 600 | those having $K_d$ values of 0, 0.25, 0.4 and 0.6 contained in each of the various heat treated solutions was determined. The results of these tests are summarized in the following Table I.

TABLE I

| | TEMP. | | | % Peak Height | | | |
|---|---|---|---|---|---|---|---|
| CONC. | (°C.) | TIME | pH | $K_d = 0$ | $K_d = 0.25$ | $K_d = 0.4$ | $K_d = 0.6$ |
| 5% | 60* | 3 M | 4.58 | 1 | 18 | 77 | 4 |
| | 75 | 1 wk. | 4.07 | 0 | 6 | 85 | 9 |
| | Reflux | 1 hr. | 4.41 | 0 | 11 | 85 | 5 |
| 10% | 60 | 3 M | 4.41 | 1 | 29 | 66 | 4 |
| | 75 | 1 wk | 4.30 | 2 | 25 | 69 | 4 |
| | Reflux | 1 hr. | 4.38 | 8 | 23 | 65 | 4 |
| 15% | 60 | 3 M | 4.33 | 3 | 43 | 52 | 2 |
| | 75 | 2 wk | 4.21 | 2 | 33 | 61 | 4 |
| | 90 | 2 wk | 4.21 | 1 | 30 | 66 | 3 |
| | Reflux | 24 hr. | — | 3 | 29 | 66 | 3 |
| 20% | 60 | 3 M | 4.25 | 9 | 48 | 39 | 5 |
| | 75 | 2 wk | 4.18 | 4 | 43 | 49 | 5 |
| | 90 | 2 wk | 4.09 | 3 | 36 | 56 | 4 |
| | Reflux | 24 hrs. | — | 3 | 40 | 52 | 5 |
| 25% | 60 | 4.8 M | 4.00 | 41 | 39 | 17 | 4 |
| | 75 | 2 wk | 4.07 | 11 | 48 | 37 | 4 |
| | 90 | 2 wk | — | 6 | 49 | 43 | 3 |
| 25% | RT | 0 (initial) | 4.26 | 71 | 18 | 6 | 4 |

*Solutions stored at 60° C. change slowly. It appears that some of these solutions have not yet equilibrated.

With these settings the inlet and the outlet temperatures of the spray dryer are 170° C. and 90° C. respectively.

4. Collect the solid powder in a jar. Cap it to avoid exposure to moisture.

ANALYSIS AND CALCULATION

The amount of $K_d=0.4$ species is determined by employing gel filtration chromatography (GFC) using 50 cm×1 cm Sephadex G-25 columns and 0.2M KCl—3.5×10$^{-3}$N HCl eluant pumped at a rate of 0.4 ml/min. The polymeric species are detected by a refractive index detector. The eluted GFC fractions are collected throughout the run and analyzed for aluminum by Inductively Coupled Plasma (ICP) spectroscopy using yttrium as an internal standard. The chromatographic peaks are identified by their partition coefficients which are calculated by employing the following equation:

$$K_d = (V_e - V_o)/(V_t - V_o)$$

where
$K_d$ is the partition coefficient of the peak
$V_e$ is the elution volume of the peak
$V_o$ is the void volume of the column
$V_t$ is the total bed volume The amount of aluminum content of each peak is computed as a percent of the peak height to the total peak heights, i.e., $$\text{Percent Aluminum of a peak} = \frac{\text{Aluminum Peak Height}}{\text{Sum of Aluminum Peak Heights}} \times 100$$

To study the effect of the concentration of aluminum chlorhydroxide solution, the time of heating and the temperature of heating on the distribution of various molecular species of aluminum chlorhydroxide a series of 5/6 basic aluminum chlorides were prepared ranging in concentration from 5% to 25% by weight. These were heated at various temperatures and various periods of time. The % of each of the molecular species i.e.

As is quite evident from the Table when 5% solutions are used as compared with the rest of the solutions, the percent of desired molecular species $K_d=0.4$ obtained is significantly higher. Furthermore, although heating a 5% solution of 5/6 basic aluminum chloride at 75° C. gave a product that had the $K_d=0.4$ molecular species at a level of 85% to do this required that the product be heated for a week. In contrast to this when the 5% solution was heated to reflux the same level of $K_d=0.4$ molecular species (85%) was reached in 1 hour.

To test the antiperspirant efficacy of a series of products containing a variety of quantities of the several molecular species of aluminum chlorhydroxide (i.e. $K_d=0.4$ to $K_d=0.6$) four products were tested using the conventional procedure for determining the degree of perspiration inhibition obtained with each product. The results of these tests are summarized in Table II below.

TABLE II

| | | % Peak Height (Refractive Index) | | | | |
|---|---|---|---|---|---|---|
| Product Tested | Actual Amt. Aluminum Chlorhydroxide Applied (mg) | $K_d$ 0.0 | $K_d$ 0.25 | $K_d$ 0.4 | $K_d$ 0.6 | Estimated % Inhibition (3rd Treatment Day) |
| A | 52 | 0 | 34 | 62 | 4 | 38 |
| B | 155 | 49 | 25 | 15 | 11 | 27 |
| C | 49 | 76 | 24 | — | — | 13 |
| D | 49 | 8 | 33 | 59 | — | 31 |

As will be clear from this Table those products having the higher content of molecular species $K_d=0.4$ (Products A and D) proved to be more effective as antiperspirants.

What is claimed is:

1. A process for preparing an aluminum chlorhydroxide product containing from about 77% to about 85% of an aluminum chlorhydroxide molecular species having a $K_d$ value equal to about 0.4 comprising heating an about 5% aqueous solution of aluminum chlorhydroxide at a temperature of from about 60° C. to about 132° C. and for a period of from about 30 minutes to about three months to produce a reaction product, spray drying the reaction product so produced, and recovering the powdered aluminum chlorhydroxide product.

2. The process according to claim 1, wherein the heating of said solution is in a closed vessel and under pressure.

3. The process according to claim 2, wherein the pressure is up to about 35 psig.

4. The process according to claim 3, wherein the pressure is from about 25 to about 35 psig.

5. The process according to claim 1, wherein the aluminum chlorhydroxide is 5/6 basic aluminum chloride.

6. The process according to claim 2 wherein the aluminum chlorhydroxide is 5/6 basic aluminum chloride.

7. The aluminum chlorhydroxide product made by the process of claim 1, 2, 3, 4, 5 or 6.

8. The process of claim 1 wherein the solution is heated at about 75° C. for about one week.

9. The aluminum chlorhydroxide product produced by the process of claim 8.

10. The process of claim 1 wherein the solution is heated at about reflux temperature for about one hour.

11. The aluminum chlorhydroxide products produced by the process of claim 10.

* * * * *